(12) United States Patent
Britton et al.

(10) Patent No.: US 8,425,596 B2
(45) Date of Patent: Apr. 23, 2013

(54) RETINAL INSTRUMENT

(75) Inventors: Charles L. Britton, Alcoa, TN (US);
Brian R. D'Urso, Clinton, TN (US);
Edward Chaum, Memphis, TN (US);
John T. Simpson, Clinton, TN (US);
Justin S. Baba, Knoxville, TN (US); **M.
Nance Ericson**, Knoxville, TN (US);
Robert J. Warmack, Knoxville, TN
(US)

(73) Assignees: UT-Battelle, LLC, Oak Ridge, TN (US);
**University of Tennessee Research
Foundation**, Knoxville, TN (US)

( * ) Notice: Subject to any disclaimer, the term of this patent is extended or adjusted under 35 U.S.C. 154(b) by 820 days.

(21) Appl. No.: 12/052,992

(22) Filed: Mar. 21, 2008

(65) Prior Publication Data

US 2009/0240271 A1    Sep. 24, 2009

(51) Int. Cl.
*A61F 2/16* (2006.01)
(52) U.S. Cl.
USPC ............................................. 623/6.12
(58) Field of Classification Search .............. 600/564,
600/566, 567; 606/161, 184–186, 189; 604/117,
604/173, 272
See application file for complete search history.

(56) References Cited

U.S. PATENT DOCUMENTS

| | | | |
|---|---|---|---|
| 6,451,240 B1 * | 9/2002 | Sherman et al. | 264/504 |
| 7,150,904 B2 | 12/2006 | D'Urso et al. | |
| 2002/0042589 A1 * | 4/2002 | Marsoner | 604/46 |
| 2002/0151774 A1 | 10/2002 | Soller et al. | |
| 2003/0050602 A1 * | 3/2003 | Pettis et al. | 604/117 |
| 2005/0261632 A1 * | 11/2005 | Xu | 604/173 |
| 2006/0251859 A1 | 11/2006 | D'Urso | |
| 2008/0221407 A1 * | 9/2008 | Baker | 600/309 |
| 2009/0093775 A1 * | 4/2009 | Raju et al. | 604/272 |

* cited by examiner

*Primary Examiner* — Ryan Severson
*Assistant Examiner* — Ashley Cronin
(74) *Attorney, Agent, or Firm* — Scully, Scott, Murphy & Presser, P.C.

(57) ABSTRACT

In one embodiment, the present invention provides a method of removing scar tissue from an eye that includes inserting a device including an array of micro-rods into an eye, wherein at least one glass micro-rod of the array of glass micro-rods includes a sharp feature; contacting a scar tissue with the array of micro-rods; and removing the array of micro-rods and the scar tissue from the eye. In another embodiment, the present invention provides a medical device for engaging a tissue including and an array of glass micro-rods, wherein at least one glass micro-rod of the array of glass micro-rods includes a sharp feature opposite a base of the array of glass micro-rods that is connected to the cannula, wherein the sharp feature of the at least one micro-rod is angled from a plane that is normal to a face of the base of the array of glass micro-rods.

16 Claims, 5 Drawing Sheets

RETINAL INSTRUMENT

STATEMENT REGARDING FEDERALLY SPONSORED RESEARCH OR DEVELOPMENT

This invention was made with Government support under Contract No. DE-AC05-00OR22725 awarded by the United States Department of Energy. The Government has certain rights in this invention.

FIELD OF THE INVENTION

The present invention in one embodiment relates to surgical instruments. In another embodiment, the present invention relates to a method of removing tissue, such as scar tissue from an eye.

BACKGROUND OF THE INVENTION

Repair of macular pucker or epiretinal membrane (ERM) is accomplished through vitreoretinal surgery. Using microsurgical instruments, a procedure known as vitrectomy or removal of vitreous gel from the posterior chamber of the eye is performed. Specialized microsurgical instruments are then used to gently peel and remove the scar tissue from the surface of the retina, relieving the traction and reducing the distortion to the retinal surface. The membrane peel involves identifying the outer edge of the membrane and creating a dissection plane with the use of blunt-tipped pic, bent needle, or diamond dusted silicone cannula. The epiretinal membrane may be gently lifted off the retinal surface with the use of a pic or fine forceps. This procedure is relatively straight forward if the edge of the epiretinal membrane is visible.

When the edge is difficult to identify the surgeon can create a slit on the thickest part of the epiretinal membrane with a straight microvitreoretinal blade and using the opening produced by this slit as an edge to begin peeling of the epiretinal membrane from the retina. The peeling is performed moving the forceps in a circular motion. Petechial hemorrhage along the internal retinal surface may be seen as the membrane is peeled off the retina. Significant bleeding may occur when an underlying vessel is damaged as a strongly adherent epiretinal membrane is peeled from the retina. Postoperative complications include cystoid macular edema (CME), retinal phototoxicity, endophthalmitis, subretinal neovascularization, and recurrent epiretinal membrane.

An alternative approach that has gained favor since the introduction of 25-gauge (25 g) instrumentation is direct peeling of the internal limiting membrane of the retina, which may be referred to as the internal limiting membrane (ILM) peel. The ILM is innermost surface of the retina and is comprised of a thin lamina. In an ILM PEEL, an edge in the ILM is created with a sharp microvitreoretinal blade and an ILM maculorhexis performed with fine forceps, peeling away both the ILM and the overlying adherent ERM.

Removal of epiretinal membrane from the retina by manual peeling is technically demanding and difficult. The retina is between 160 microns and 240 microns thick and is generally transparent. The epiretinal membrane that is grown on the retinal surface is thinner than the retina typically 10-30 microns thick as measured by optical coherence tomography (OCT) and is often friable. This anatomical relationship results in extremely minute tolerances in manual attempt to engage the membrane. The application of too much pressure or misalignment of the position of the tip of the peeling instrument may result in a vision threatening injury that can result from damaging a portion of the retina, such as a region of the fovea.

SUMMARY OF THE INVENTION

The present invention provides medical devices and methods for removing scarred tissue, particularly scarred tissue from an eye. The medical devices of the present invention are characterized by an array of micro-needles or micro-spikes, where the array is capable of engaging a scar tissue including, for example, engaging a large area of the scar tissue and to a desirable depth. The medical devices of the present invention permit removal of the scar tissue, for example, in a smooth peeling fashion, or "en bloc" by acting like a surgical Velcro.

In one embodiment, the method of the present invention includes:

inserting a device including an array of glass micro-rods into an eye, at least one of the glass micro-rods including at least one sharp feature;

contacting a scar tissue or an underlying tissue on which the scar tissue is present with the array of glass micro-rods; and removing the array of glass micro-rods from the eye, wherein the scar tissue is engaged to the array of glass micro-rods or the array of glass micro-rods is engaged to the underlying tissue on which the scar tissue is present.

In one embodiment, the scarred tissue that is being removed from the eye is present on a retina. In one embodiment, the method further includes measuring the thickness of the scar tissue before inserting the device including the array of glass micro-rods into the eye, and providing an array of glass micro-rods having a micro-rod length that is less than or equal to the thickness of the scar tissue. In one embodiment, the measuring of the thickness of the scarred tissue includes optical coherence tomography (OCT) or Heidelberg retinal tomopgrapy.

In one embodiment, each of the sharp features of the plurality of glass micro-rods has a uniform length. The term uniform length means that the each of the sharp features in the array of micro-rods has substantially the same length. In one embodiment, the sharp feature of each glass micro-rod extends has a length that extends the entire length of the glass micro-rod. In another embodiment, the sharp feature of each glass micro-rods extends a portion of the length of the glass micro-rod. In one embodiment, the length of the sharp features is selected to penetrate and retain the scar tissue to a fixed depth without penetrating the underlying tissue of the eye, such as the retina. In another embodiment, the glass micro-rods of the array of glass micro-rods has a uniform dimension.

In one embodiment, the device further includes a cannula that is engaged to the base of the array of micro-rods. In one embodiment, in which at least one sharp feature corresponding to each glass micro-rod of the array of glass micro-rods is opposite the base of the array of micro-rods, the sharp feature of the at least one micro-rods is angled from a plane that is normal to a face of the base of the array of glass micro-rods.

In another embodiment, the device further includes a cannula engaged to the base of the array of micro-rods, wherein the length of the sharp feature is normal to the base of the array of micro-rods, wherein a plane parallel to the face of the base of the array of micro-rods that is engaged to the cannula is angled relative to a direction that is parallel to the length of the cannula.

In another embodiment, the device further includes a cannula engaged to the base of the array of micro-rods, wherein the length of the sharp feature is normal to the base of the array of micro-rods, wherein the face of the base of the array of micro-rods that is engaged to the cannula is angled relative to a direction that is parallel to the length of the cannula.

In another embodiment, in which the device further includes a cannula engaged to the base of the array of micro-rods, the length of the sharp feature or sharp features is normal to the base of the array of micro-rods, wherein the face of the base of the array of micro-rods that is engaged to the cannula is angled relative to a direction that is parallel to the length of the cannula, wherein at least a portion of the cannula is curved.

In one embodiment, contacting the scar tissue or the underlying tissue on which the scar tissue is present means that the scar tissue or underlying tissue is engaged by the sharp feature or sharp features of the at least one glass micro-rod of the array of glass micro-rods. In one embodiment, the engagement of the sharp feature or sharp features of the array of glass micro-rods is a hook type engagement, wherein the length of the sharp feature or sharp features does not penetrate to a depth that is greater than the thickness of the scar tissue or underlying tissue that is being removed. In one embodiment, the sharp feature or sharp features is an angled sharp feature. In one embodiment, contacting the scar tissue means that as the array of glass micro-rods is traversed along a first direction, the angled sharp features engage the scar-tissue or the underlying tissue on which the scar tissue is present, wherein the angled sharp features hook or penetrate into the scar tissue or underlying tissue. In one embodiment, as the array of glass micro-rods is traversed along a second direction that is substantially opposed to the first direction, the array is traversed so that the angled sharp features of the array of glass micro-rods do not hook or penetrate into the scar tissue or the underlying tissue on which the scar tissue is present. Instead, when traversed along the second direction the sharp features glide atop the scar tissue. This mechanism allows for the medical device to be selectively positioned on the scar tissue or the underlying tissue on which the scar tissue is present without damaging the non-targeted structures of the eye where the scar tissue is not present, such as the retina, wherein once the array of glass micro-rods is in the desired location the sharp features may be engaged to the scar tissue or underlying tissue on which the scar tissue is present by traversing the array of glass micro-rods in a direction that enables the angled sharp features to hook or penetrate into the scar tissue or underlying tissue and peel the scarred tissue from the eye, e.g., peel the scar tissue from the retina of the eye.

In one embodiment, contacting the scar tissue with the array of micro-rods includes engaging the sharp feature or sharp features of the micro-rods to a central portion of the scarred tissue. In this embodiment, in which the micro-rods are oriented in a 30 degree to 45 degree angle circumferentially around the tip of the instrument, contacting the scar tissue with the array of micro-rods is achieved by rotating the array of micro-rods about an axis that is substantially perpendicular to the surface of the scarred tissue. In one embodiment, removing the scar tissue from the eye includes peeling the scarred tissue from the retina, which may be an en-bloc scar tissue removal. By "en bloc" it is meant that the scarred tissue is removed in a single piece, i.e., in its totality, as opposed to the scarred tissue being removed in a plurality of pieces.

In another aspect of the present invention, a medical device is provided for removing tissue from an eye that includes an array of angled glass micro-rods. In one embodiment, the large array of angled glass micro-rods may be arranged in a pad geometry, and may be referred to as surgical Velcro. In one embodiment, the large array of angled glass micro-rods enables the device to be traversed across the scar tissue in a first direction without engaging the scar tissue, hence essentially gliding over the scar tissue, and to engage the scar tissue when traversed along a second direction, wherein the second direction substantially opposes the first direction. In one embodiment, the medical device includes:

a cannula; and an array of glass micro-rods, wherein at least one glass micro-rod of the array of glass micro-rods includes a sharp feature opposite a base of the array of glass micro-rods that is connected to the cannula, wherein the sharp feature of the at least one micro-rod is angled from a plane that is normal to a face of the base of the array of glass micro-rods.

In one embodiment, the glass micro-rods include a silica containing material. In one embodiment, the glass composition is a soda lime silicate, boro silicate, and lead silicate glass. In one embodiment, the array of glass micro-rods include a plurality of glass micro-rods, wherein adjacent glass micro-rods are separated by a distance ranging from about 5 microns to about 40 microns In one embodiment, at least one of the glass-micro-rods of the array has a length of less than 30 microns. In one embodiment, the base of the array of the glass micro-rods has a substantially circular geometry or a multi-faced geometry.

In one embodiment, the sharp feature of the at least one micro-rod is angled to provide a barb. In one embodiment, the sharp feature of the at least one micro-rod is angled from the plane that is normal to the face of the base of the array of glass micro rods, by an angle ranging from about 30 degrees to about 60 degrees.

In another embodiment, a medical device is provided for removing tissue from an eye including an array of glass micro-rods having a sharp feature that is configured to be normal to a base of the glass mirco-rods, wherein the base of the glass micro-rods is angled at the attachment of cannula to the array of glass micro-rods. In one embodiment, the medical device includes:

a cannula; and an array of glass micro-rods, wherein at least one glass micro-rod of the array of glass micro-rods includes a sharp feature opposite a base of the array of glass micro-rods that is connected to the cannula, the sharp feature of the at least one micro-rod is normal to a face of the base of the array of glass micro-rods, wherein the face of the base of the array of micro-rods that is engaged to the cannula is angled relative to a direction that is parallel to a length of the cannula.

In another embodiment, a medical device is provided for removing tissue from an eye including an array of glass micro-rods having a sharp feature that is configured to be normal to a base of the glass mirco-rods, wherein the cannula includes a curvature to angle the array of glass micro-rods. In one embodiment, the medical device includes:

a cannula; and an array of glass micro-rods, wherein at least one glass micro-rod of the array of glass micro-rods includes a sharp feature opposite a base of the array of glass micro-rods that is connected to the cannula, the sharp feature of the at least one micro-rod is normal to a face of the base of the array of glass micro-rods, wherein at least a portion of the cannula is curved.

BRIEF DESCRIPTION OF THE DRAWINGS

The following detailed description, given by way of example and not intended to limit the invention solely thereto, will best be appreciated in conjunction with the accompanying drawings, wherein like reference numerals denote like elements and parts, in which.

DETAILED DESCRIPTION OF THE INVENTION

Figure 1:
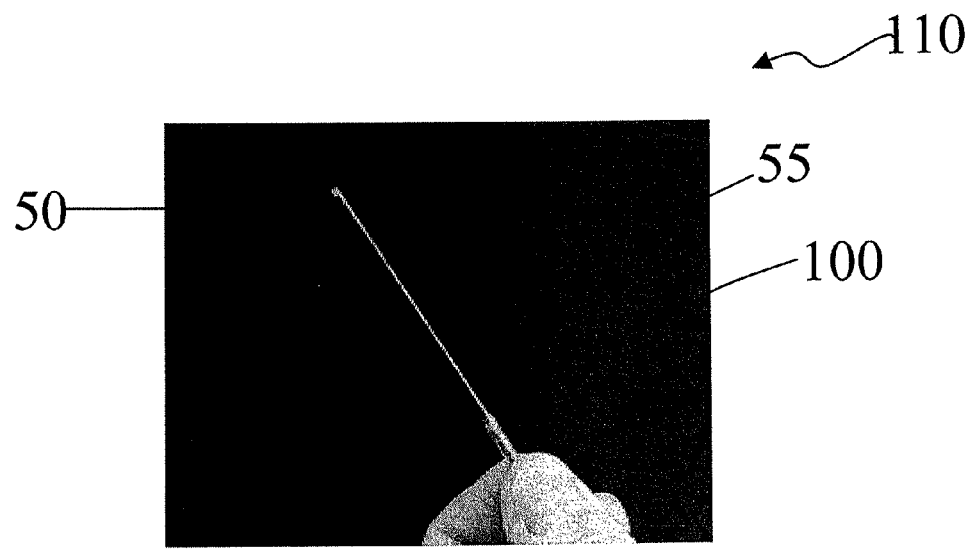
FIG. 1 is a pictorial view of one embodiment of a medical device for removing tissue from an eye, in accordance with the present invention.

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

The embodiments of the present invention relate to medical devices and methods for removing tissue, such as removing scar tissue from an eye. When describing the following structures and methods, the following terms have the following meanings, unless otherwise indicated.

The term "glass" denotes a non-crystalline solid.

The term "micro-rod" denotes a structure having a height of less than 100 microns and having an aspect ratio of length to width on the order of approximately 5:1 or greater, having a height no greater than 100 microns wherein a cross section perpendicular to the height is multi-sided or of arcular geometry.

The phrase "sharp feature" is defined herein to mean a tapered structure that terminates into a point. In one embodiment, the sharp surface feature tapers from a base portion having a first cross sectional area to a point portion opposite the base portion having a reduced cross sectional area that is no more than 30% of the first cross sectional area, such as 25%, 20%, 15%, 10%, 8%, 6%, 5%, 4%, 3%, 2%, 1%, or less than 1% of the first cross sectional area. In one embodiment, the sharp surface feature is a spike. In one embodiment, a spike has a base with a circumferential geometry and a tip with a circumferential geometry.

The term "cannula" means a tube that can be inserted into a body cavity, organ or duct.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper", "lower", "right", "left", "vertical", "horizontal", "top", "bottom", and derivatives thereof shall relate to the invention, as it is oriented in the drawing figures.

The present invention in one embodiment is directed to removing scarred tissue from the eye. A macular pucker is one form of scar tissue that forms on the surface of the retina, typically being in the macula, and typically located in the center of the retina. The formation of macular puckers can cause blurred and distorted central vision. The formation of macular puckers may result from a condition known as vitreous detachment. The eye's interior is filled with a vitreous, gel-like substance that fills about 80 percent of the eye. The vitreous contains on the order of millions of fine fibers that are attached to the surface of the retina. As the eye ages, the vitreous shrinks and pulls away from the retina typically resulting in the formation of microscopic damage to the retina's surface. As this occurs, the retina begins a healing process to the damaged area and forms scarred tissue, i.e., epiretinal membrane (ERM), on the surface of the retina. ERMs are hypocellular and collagenous proliferations. ERMs represent a form of proliferative vitreoretinopath (PVR) caused by cells that are released into the vitreous cavity and subsequently become attached to the retina. These cells proliferate and secrete collagen to form sheets of membranes over the retina. Because of the presence of contractile proteins in these cells, they may exhibit myofibroblastic properties that enable them to change shape within the collagenouse scaffold of the membrane and exert traction on the retina.

When this focal area of damage or irritation occurs in the macular region, the retina initiates a healing response with mobilization and migration of cells found within the retina itself, which tend to spread outward along the surface of the retina, in an attempt to heal the areas of damage. This scarred tissue is attached to the retina surface. When the scarred tissue contracts it can cause the retina to wrinkle and the central vision degrades. Hereafter, macular puckers and epiretinal membranes (ERM) are referred to as scarred tissue. Other examples of scarred tissue that may be removed from the eye using the method and structures of the present invention include proliferative vitreoretinopathy, fibrovascular proliferation, and adherent posterior hyaloid tissue. It is noted, that the above examples of scar tissue are provided for illustrative purposes only and that other types of scarred tissue have been contemplated and are within the scope of the invention.

In one embodiment, the present invention removes the scarred tissue by removing the underlying tissue on which the scarred tissue is present. In one embodiment, the underlying tissue that the scarred tissue is present on is a thin lamina layer on an inner surface of the retina. In one embodiment, the lamina layer on the inner surface of the retina that provides the underlying tissue on which the scar tissue is present is the internal limiting membrane (ILM).

FIG. 1 depicts one embodiment of a medical device 100 for removing tissue from an eye, such as scar tissue from the retina of the eye. In one embodiment, the medical device 100 includes an array of glass micro-rods 50 that are positioned at the insertion end 110 of a cannula 55 for engaging the scarred tissue. More specifically, in one embodiment, the array of glass micro-rods is positioned so that once the cannula 55 is inserted into the eye the array of glass micro-rods 50 may be manipulated to contact and engage the scarred tissue, wherein once the array of glass micro-rods 50 is engaged to the scarred tissue the medical device 100 is removed from the eye, hence removing the scar tissue.

In another embodiment, the array of glass micro-rods 50 may be manipulated to separate an underlying tissue that the scarred tissue is present on from the retina. In this embodiment, the underlying tissue is separated from the retina in a peeling process. The underlying tissue is separated from the retina. The scar tissue attached to the underlying tissue is removed from the retina. This process may also be referred to as an ILM peel.

Figure 2:
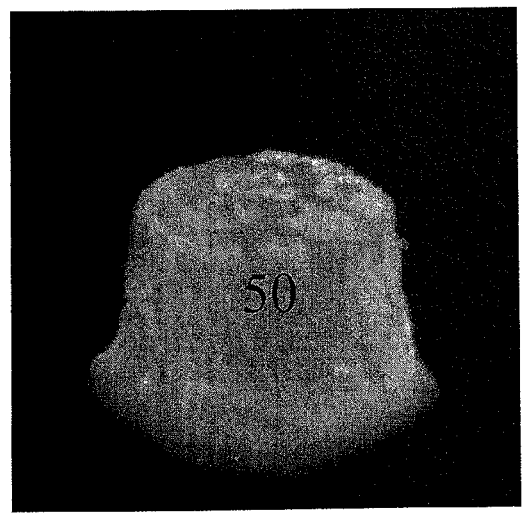
FIG. 2 is a magnified perspective view of one embodiment of a glass micro-rod array as used in a medical device for removing tissue from an eye, in accordance with the present invention.

FIG. 2 is a magnified perspective view of one embodiment of an array of glass micro-rods 50. In one embodiment, the array of glass micro-rods 50 may be provided by a pad having a width equal to about 1 mm to about 5 mm, and a length equal to about 1 mm to about 3 mm, wherein the pad has on the order of approximately 350,000 or less micro-rods.

In one embodiment, in which the pad diameter is on the order of about 3 mm with a spacing between adjacent micro-rods on the order of about 5 microns, the resulting number of glass micro-rods is on the order of 350,000. In another embodiment, for a pad diameter on the order of about 1 mm with a spacing between adjacent micro-rods on the order of about 100 microns, the resulting number of glass micro-rods can be on the order of about 100 glass micro-rods.

Referring to FIG. 1, in one embodiment, the insertion end 110 of the medical device 100 includes a 25 gauge tip on which the array of glass micro-rods 50 is present, wherein the array of glass micro-rods 50 includes at least one glass micro-rod that includes a sharp feature that is angled. In one embodiment, the glass rods have an aspect ratio of length to width on the order of about 10:1 or greater. In another embodiment, the glass rods have an aspect ratio of length to width on the order of about 100:1.

In one embodiment, the sharp feature 51 is a spike. In one embodiment, a spike has a base with a circumferential geometry and a tip with a circumferential geometry. In another embodiment, the base portion 52 may have a multisided geometry, such as a hexagonal shape.

Figure 3:
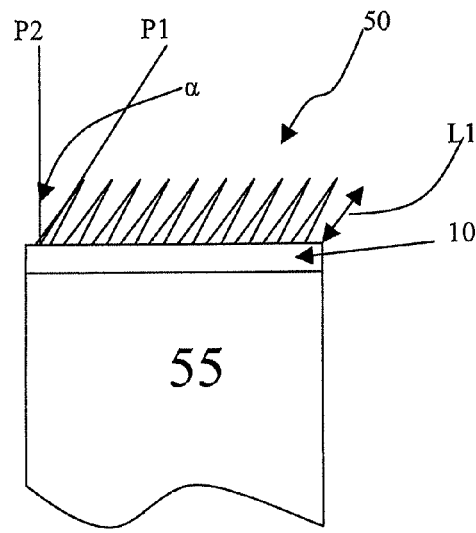
FIG. 3 is a side cross sectional view of one embodiment of a medical device for removing tissue from an eye, in accordance with the present invention.

FIG. 3 is a side cross-sectional view of an array of glass micro-rods, in which the sharp feature 51 of each glass micro-rod is angled. In one embodiment, the angle at which each sharp feature 51 is positioned may be defined by the angle α at the intersection of a plane parallel $P_1$ to the length $L_1$ of the sharp feature 51 of the glass micro-rod and a plane $P_2$ that is normal to the base 10 of the array of micro-rods 50. In one embodiment, the base 10 of the array of glass micro-rods 50 is connected to the cannula 55. In one embodiment, the length $L_1$ of the sharp feature 51 extends from the base portion 10 of the glass micro-rod to the point portion 53 of the glass micro-rod. It is noted that although, the sharp feature 51 is depicted in the supplied figures as extending the entire length of each of the glass micro-rods, embodiments of the present invention have been contemplated that include where the sharp feature 51 only extends along a portion of the length of the glass micro-rods.

Still referring to FIG. 3, in one embodiment, the length $L_1$ of the sharp feature 51 may be angled α from about 15° to about 90° from a plane $P_2$ that is normal to a face of the base 10 of the array of glass micro-rods 50. In another embodiment, the length $L_1$ of the sharp feature 51 may be angled from about 15° to about 50° from a plane $P_2$ that is normal to a face of the base 10 of the array of glass micro-rods 50

Figure 4:
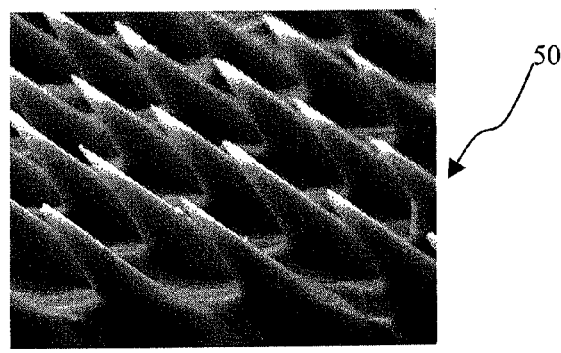
FIG. 4 is a micrograph of one embodiment of a glass micro-rod array of angled glass micro-rods, in accordance with the present invention.

FIG. 4 is a magnified view of one embodiment of an array of glass micro-rods 50, in which the sharp feature of the glass micro-rods are angled approximately 45 degrees, as measured by the angle α defined at the intersection of a plane parallel to the length of the sharp feature of the glass micro-rod and the plane that is normal to the face of the base of the array of glass micro-rods 50.

Figure 5:
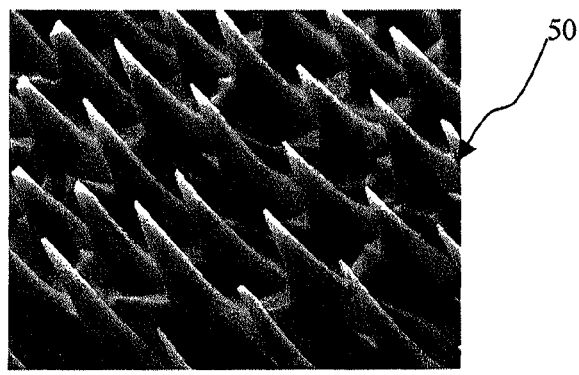
FIG. 5 is a micrograph of another embodiment of a glass micro-rod array of angled glass micro-rods, in accordance with the present invention.

FIG. 5 depicts a scanning electron microscope image of one embodiment of a glass micro-rod, in which the sharp feature of the glass micro-rods are angled approximately 30 degrees, as measured by the angle defined at the intersection of a plane parallel to the length of the sharp feature of the glass micro-rod and the plane that is normal to the face of the base of the array of glass micro-rods 50.

Figure 6:
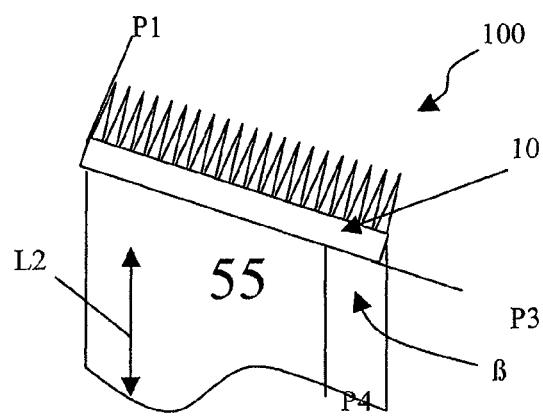
FIG. 6 is a side cross sectional view of another embodiment of a medical device for removing tissue from an eye, in accordance with the present invention.

FIG. 6 depicts another embodiment of a medical device 100 for removing scar tissue from an eye including an array of glass micro-rods 50 having a sharp feature 51 that is positioned to be normal to a base 10 of the array of glass mirco-rods 50, wherein the base 10 of the array of glass micro-rods 50 is angled at the attachment of cannula 55 to the array of glass micro-rods 50. In one embodiment, the medical device 100 includes a cannula 55 and an array of glass micro-rods 50, wherein at least one glass micro-rod of the array of glass micro-rods includes a sharp feature 51 opposite a base 10 of the array of glass micro-rods 50 that is connected to the cannula 55, the sharp feature 51 of the at least one micro-rod is normal to a face of the base 10 of the array of glass micro-rods 50, wherein the face of the base 10 of the array of glass micro-rods 50 that is engaged to the cannula 55 is angled relative to a direction that is parallel to a length L2 of the cannula 55. The term "normal" as used herein means that the plane P1 parallel to the length L1 of the sharp feature 51 and the plane P3 that is parallel to the width of the base 10 of the array of glass micro-rods 50 is approximately 90 degrees.

In one embodiment, when the sharp features 51 are normal to the base of the array of glass micro-rods 50, the base 10 of the array of glass micro-rods 50 is angled relative to cannula 55 to provide an angle β at the intersection of the plane P3 parallel to the width of the base 10 of the array of glass micro-rods 50 and the plane P4 parallel to the length L2 of the cannula 55 that ranges from about 0° to about 70. In another embodiment when the sharp features 51 are normal to the base 10 of the array of glass micro-rods 50, the base 10 of the array of glass micro-rods 50 is angled relative to cannula 55 to provide an angle β at the intersection of the plane P3 parallel to the width of the base 10 of the array of glass micro-rods 50 and the plane P4 parallel to the length L2 of the cannula 55 that ranges from about 20° to about 50° from the plane $P_3$ parallel to the length L2 of the cannula 55

Figure 7:
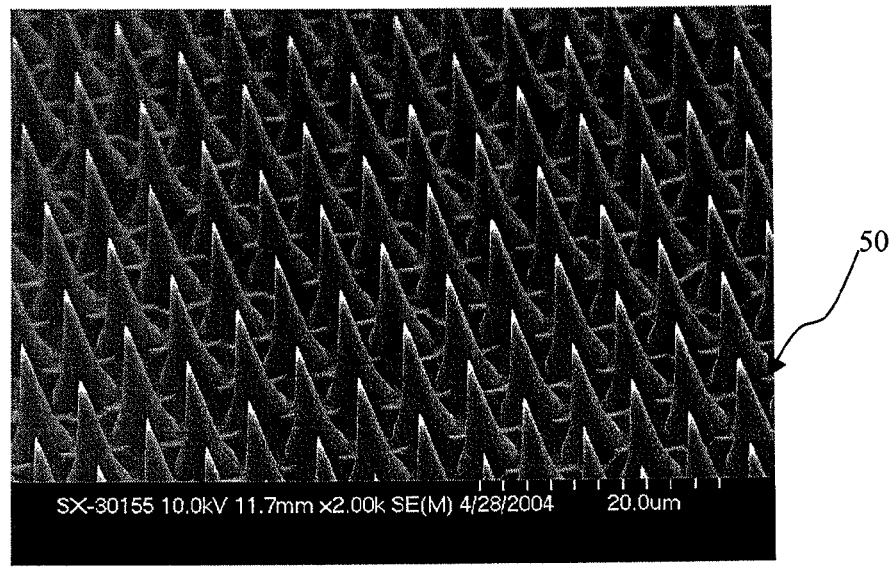
FIG. 7 is a micrograph of one embodiment of a glass micro-rod array in which the length of the glass micro-rods is normal to the base of the array of glass micro-rods, in accordance with the present invention.

FIG. 7 is a magnified view of one embodiment of an array of glass micro-rods 50, in which the sharp features of the glass micro-rods are normal to the base of the array of glass micro-rods, which may also be referred to as a vertically aligned array of glass micro-rods.

Figure 8:
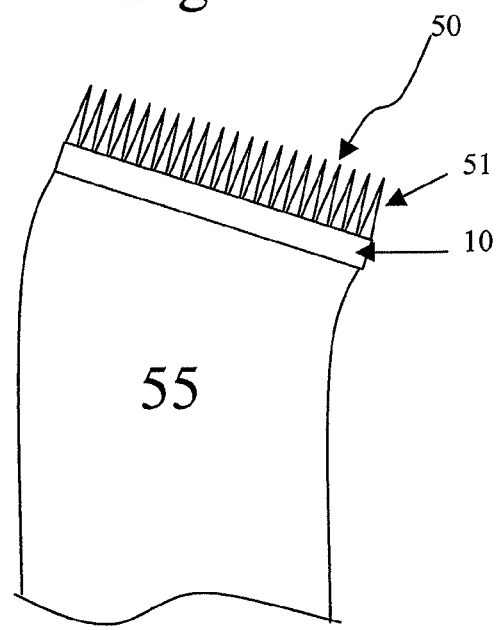
FIG. 8 is a side cross sectional view of another embodiment of a medical device for removing tissue from an eye, in accordance with the present invention.

FIG. 8 depicts another embodiment of a medical device 100 for removing tissue from an eye including an array of glass micro-rods 50 having a sharp feature 51 that is configured to be normal to a base 10 of the array of glass mirco-rods 50, wherein the cannula 55 includes a curvature to angle the array of glass micro-rods. In one embodiment, the medical device 100 includes a cannula 55; and an array of glass micro-rods 50, wherein at least one glass micro-rod of the array of glass micro-rods 50 includes a sharp feature 51 opposite a base 10 of the array of glass micro-rods 50 that is connected to the cannula 55, the sharp feature 51 of the at least one micro-rod is normal to a face of the base 10 of the array of glass micro-rods 50, wherein at least a portion of the cannula 55 is curved.

In another aspect of the present invention, a method of manufacturing a medical device is provided. In one embodiment, the sharp features of the array of glass micro-rods are made of a composite material that is etched using a selective etch process. The composite material may be made from any two components that provide suitable differential etching characteristics relative to one another. Suitable materials include, for example, glasses, metals (including alloys), ceramics, polymers, resins, and the like. In one embodiment, the composite material may include a recessive component and a protrusion component, wherein the recessive component is etched selective to the protrusion component. In one embodiment, the composite material includes a core, such as rods, and a matrix, such as cladding present on the exterior of the rod.

In one embodiment, the protrusive component is a core of the composite material. In one embodiment, the protrusive component of the composite material may be composed of glass rods composed of Corning 0120. Corning 0120 is composed of a $K_2$—O—PbO—$B_2$—$O_3$—$SiO_2$ system. It is noted that other materials may be suitable for the protrusive component, so long as the material selected etched at a slower rate than the recessive component. In one embodiment, the recessive component is present on the exterior of the core of the protrusive component. In one embodiment, the recessive component of the composite material may be composed of a cladding composed of Corning 8161. Corning 8161 is composed of about 51 wt. %, PbO, about 39 wt. % $SiO_2$, about 6 wt. % $K_2O$, and about 2 wt. % KaO. The two glasses are differentially etched such that the cladding glass is etched away from the core glass, while the core glass becomes sharpened (tapered) by the etching process. It is noted that the above glass compositions are noted for illustrative purposes only and are not intended to limit the scope of the present invention, since other compositions have been contemplated and are within the scope of the present invention. One factor that is considered in selecting glass compositions for use with the present methods and structures is that the glass compositions selected for the core, i.e., protrusive component, and the cladding, i.e., recessive component, should be "drawable", that is their softening temperatures (Tg) should overlap. In one embodiment, a carbon nanotube structure may be used, as opposed to a glass composition, to provide the micro-rods.

In one embodiment, the recessive component of the composite material is etched selective to the protrusion component. Etch selectively means that one component, i.e., the recessive component of the composite material, is etched at a faster rate than a second component, i.e., the protrusion component. In one embodiment, the etchant is composed of an organic or inorganic acid or alkali; polar, nonpolar, organic, inorganic, or mixed solvent; or mixtures of any of the foregoing. The etchant is selected to selectively etch the composite material as described herein. For example, an acid such as HF, HCl, HBr, or HI is selected to differentially etch glass compositions.

In one embodiment, the etchant is composed of a "mixed etchant system" which includes of a mixture of a plurality of etchants that provide selective etch contrast ratios when applied to the composite material. For example, in one embodiment the etchant can selectively etch one phase while the other etchant can selectively etch the other phase. One example of a mixed etchant system is a mixture of HF and HCl.

In another embodiment, a plurality of etchants can be used in a series of two or more sequential etching steps. For example, in one embodiment HF is applied to the composite material in a first etching step, rinsed away, and then HCl is applied to the composite material in a second etching step.

In one embodiment when the composite material is composed of a core, e.g., rods of a protrusive component, and a matrix, e.g., cladding material of a recessive material, prior to etching the core and the matrix are bundled into an aligned array (hereafter referred to as a bundle). In one embodiment, the matrix has a multi-sided, e.g., hexagonal, cross-sectional shape to minimize voids while the core has a circular cross-section. In another embodiment, the matrix has a circular cross-section. In one embodiment, the matrix material and core material are selected based on differential etchability, wherein the core material has a lower etch rate than the matrix material, and forms protrusive, sharp features upon etching of the composite material.

In one embodiment, the bundle can heated to a temperature sufficient to soften the materials comprising the bundle, but low enough to avoid damage, decomposition, or other deleterious changes. In one embodiment, the bundle is then drawn along the axis of the bundled rods to fuse and reduce the diameter of the bundle. In one embodiment, the drawn bundle has reduced size matrix material and core material.

The drawn bundle is cut transversely into sections that can be re-bundled to increase the number of core material cores in the cross-section thereof. In a following process step, the bundle can then be drawn again. In one embodiment, it is noted that a twice-drawn bundle has further reduced size matrix material and core material. The twice-drawn bundle may then be cut transversely into sections that are re-bundled to further increase the number of cores in the cross-section thereof. It is noted that the process of bundling, drawing, and cutting can be performed a single time or repeated many times until the desired diameter and spacing of the core material is obtained. In one embodiment, after the final draw (which may be the first draw), the bundle can be cut, bundled, and fused in order to obtain a larger diameter bundle.

In one embodiment, in which the fused fibers are aligned parallel to the axis of the bundled rod, if the rod is cut perpendicular to this axis, the subsequently etched glass micro-rods will be normal to the base surface. In another embodiment, cutting the rod at any other angle will cause the subsequently etched glass micro-rods to deviate from the normal direction by the angle at which the rod is cut.

Subsequently, in one embodiment, one or both of the cut (composite) surfaces of the bundle are etched to create an array of sharp features composed of core material on one or both sides of the cut bundle. The composite surface can be contacted with an etchant, (HF, for example), which etches the matrix material (recessive component) faster than the core material (protrusive component). The etching continues until the matrix material is etched back to the desired depth, leaving some of the core material protruding from the surface. The result is that the core material is sharpened to a cone-shaped spike that provides the sharp feature 51 that extends from a base 10. In one embodiment, the aspect ratio of the spike is dependent on the ratio of the matrix material and core material etch rates. Hereafter, the composite material that has been etched to provide the sharp features that extend from the base is referred to as the array of glass micro-rods.

In a following step, the base of the array of glass micro-rods is connected to the cannula. In one embodiment, the attachment of the array glass micro-rods is connected to the cannula by adhesive. In one embodiment in which the sharp feature of the array of glass micro-rods are positioned normal to the base of the array of glass micro-rods, the base of the cannula may be angled relative to cannula to provide an angle β at the intersection of the plane parallel to the length of the sharp features and the plane parallel to the length of the cannula. In one embodiment, the cannula has a diameter that is suitable for insertion into on eye. In one embodiment, the cannula has a diameter of 25-20 gauge or less. In another embodiment, the cannula has a diameter of 3 mm or less. In one embodiment, a fiber optic is contained within the cannula, wherein the fiber-optic glass fiber that illuminates the insertion portion of the device.

In one embodiment, the medical device of the present invention is suitable for engaging, i.e., hold and not just tear, the scarred tissue from a central portion of the scarred tissue. In one embodiment, the medical device is soft enough to engage the scarred tissue without putting undue pressure on the retina. In one embodiment, the insertion portion of the medical device has dimensions allowing for the array of glass micro-rods to be able to pass through an incision in the eye wall being less than 20 gauge in diameter. In one embodiment, the medical device includes sharp features of a specified depth (depending on the ERM or ILM so as to adhere to, i.e. penetrate and retain, the scarred tissue without engaging the retina of the eye. In another embodiment the medical device is fabricated in a thin sheet so as to engage a large surface of the scarred tissue en bloc. In one embodiment, the medical device is sterilizable, as well as disposable.

In another aspect, the present invention provides a method of removing scarred tissue from an eye using the above-described medical devices 100. In one embodiment, the method of removing the scarred tissue 21 includes inserting a device including an array of glass micro-rods 50 into an eye, wherein at least one glass micro-rod of the array of glass micro-rods 50 includes a sharp feature; contacting a tissue 21 with the array of glass micro-rods 50; and removing the array of glass micro-rods 50 and the tissue from the eye.

Figure 9:
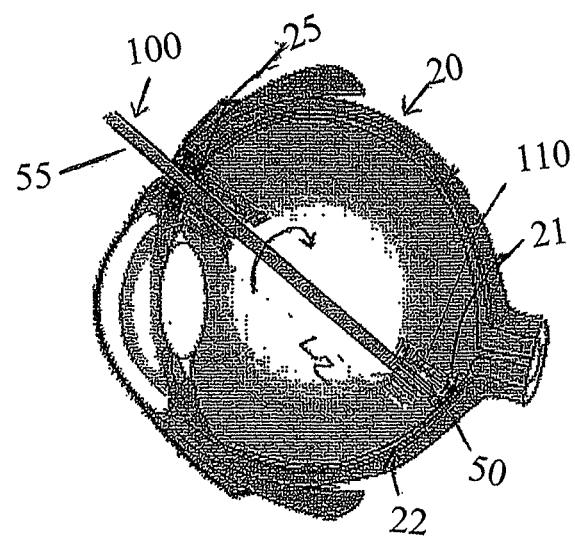
FIG. 9 is a side cross-section view depicting one method for removing a tissue from an eye, in accordance with the present invention.

Referring to FIG. 9, in one embodiment of the present invention, the sharp feature of the array of glass mirco-rods 50 hook into the scar tissue that has grown on the retina and pull the scar tissue from the retina. More specifically, in one embodiment, the array of glass micro-rods provides a plurality of sharp features, wherein the plurality of sharp features engage and retain the scar tissue in a manner that the scar tissue is removed from the underlying tissue of the eye in a single unit, e.g., with a peeling motion. In one embodiment, the plurality of sharp features provides a plurality of attachment points that are spread across the surface of the scar tissue, hence distributing the force that is applied to the scar tissue as it is being peeled from the underlying tissue of the eye. By providing a plurality of attachment points to the scar tissue, the incidence of tearing the tissue during the removal step is substantially reduced In one embodiment, the method further includes measuring the thickness of the scar tissue 21 before inserting the device including the array of glass micro-rods 50 into the eye 20, and providing an array of glass micro-rods 50 having a micro-rod length that is less than or equal to the thickness of the scar tissue 20. For example, in one embodiment, when the ERM has a thickness on the order of about 20 microns to about 30 microns, the length of the sharp feature is on the order of about 20 microns to about 30 microns to correspond to the thickness of the ERM.

In one embodiment, the method enables a surgeon to apply an array of angled sharp features 51 to engage and strip a scar tissue 20 from the retina 22, including the internal limiting membrane at defined depths selected for the patient's unique pathology based upon optical coherence tomography (OCT) imaging. Optical coherence tomography (OCT) is an interferometric, non-invasive optical tomographic imaging technique More specifically, in one embodiment, the height and pitch of the engaging sharp features of the array of glass micro-rods 50 can be engineered for desired parameters corresponding to the membrane thickness. In one embodiment, different dimensions can be selected for the length of the sharp feature 51 of the array of glass micro-rods 50 from a selection of disposable instrument choices to match the specific measured pathology of the patient based upon OCT imaging studies. In one embodiment, by matching the histopathology to the choice of instrument, the surgeon will be able to fully engage the scar tissue, but will not be able to penetrate the sensory retina. Similarly, a 20 micron instrument can be selected to use for an ILM peel to protect against injury to the underlying neurosensory retina. It is noted that the above examples are provided for illustrative purposes only and do not limit the present invention to the dimensions described above, as the present invention is applicable to removing scar tissues having any thickness.

In one embodiment, inserting the device including the array of glass micro-rods 50 into the eye includes making an incision in the eye wall, wherein the length of the incision is selected to allow a 20 gauge to 25 gauge instrument to enter the eye. Following the formation of the incision in the eye wall, the insertion portion 110 of the cannula 55 and the glass micro-rod array 55 are inserted into the eye 20. In one embodiment, contacting the scar tissue 21 with the array of glass micro-rods 50 includes engaging the sharp feature of the glass micro-rods to a central portion of the scar tissue 21. In another embodiment, contacting the scar tissue 21 with array of glass micro-rod array 50 includes contacting a perimeter portion of the scar tissue 21. In one embodiment, the vitreous gel is removed from the eye prior to insertion of the glass micro-rod array 50 to permit direct access of the array of glass micro-rods to the retina surface.

In one embodiment, depending on the geometry of (either linear or circumferential) the cannula 55 is manipulated to engage the sharp features into the scar tissue 21 either by a linear or twisting motion, i.e., rotating motion. For example, in one embodiment, contacting the scar tissue 21 with the array of glass micro-rods 50 includes rotating the array of micro-rods 50 about an axis that is substantially perpendicular to the surface of the scar tissue 21. In another embodiment, contacting the scar tissue 21 with the array of glass micro-rods 50 includes rotating R1 the array of micro-rods 50 about an axis that is substantially parallel to the length L2 of the cannula 55 after the sharp features of the array of glass micro-rods 50 have engaged the scar tissue 21.

In one embodiment in which the sharp features engage a central portion of the scar tissue, the scar tissue may be removed en bloc. In another embodiment, removing the scar tissue from the eye includes peeling the scar tissue from the retina.

The following examples are provided to further illustrate aspects of the present invention and demonstrate some advantages that arise therefrom. It is not intended that the invention be limited to the specific examples disclosed.

While the present invention has been particularly shown and described with respect to the preferred embodiments thereof, it will be understood by those skilled in the art that the foregoing and other changes in forms of details may be made without departing form the spirit and scope of the present invention. It is therefore intended that the present invention not be limited to the exact forms and details described and illustrated, but fall within the scope of the appended claims.

What is claimed:

1. A medical device for removing scarred tissue from an eye comprising:
    a cannula; and
    an array of solid glass micro-rods, wherein each solid glass micro-rod of the array of solid glass micro-rods has a length that is substantially parallel to a length of an adjacent solid glass micro-rod of the array of solid glass micro-rods, and said each solid glass micro-rod includes a sharp feature opposite a planar base of the array of solid glass micro-rods that is connected to the cannula, wherein the length of said each solid glass micro-rod is angled from a plane that is normal to the planar base of the array of solid glass micro-rods.

2. The medical device of claim 1, wherein the solid glass micro-rods comprise a silica containing material.

3. The medical device of claim 2, wherein the silica containing material comprises sodium silicate glass, boro silicate glass or leaded glass.

4. The medical device of claim 1, wherein said length of each solid glass-micro-rod is less than 60 microns.

5. The medical device of claim 1, wherein adjacent solid glass micro-rods of the array of solid glass micro-rods are separated by a distance ranging from about 5 microns to about 40 microns.

6. The medical device of claim 1, wherein the base of the array of the solid glass micro-rods has a substantially circular geometry or a multi-faced geometry.

7. The medical device of claim 1, wherein the entire length of said each solid glass micro-rod is angled from the plane that is normal to the planar base of the array of solid glass micro-rods, by an angle ranging from about 0 to about 70 degrees.

8. The medical device of claim 1, wherein each solid glass micro-rod of the array of glass micro-rods has a uniform length.

9. A method of removing scar tissue from an eye comprising:
    inserting a device according to claim 1 into an eye;
    engaging the scar tissue or underlying tissue on which the scar tissue is present with the array of solid glass micro-rods; and
    removing the array of solid glass micro-rods and the scar tissue or the underlying tissue on which the scar tissue is present from the eye.

10. The method of claim 9, wherein the scar tissue is present on a retina of the eye and removing the scar tissue from the eye includes removing the scar tissue from the retina.

11. The method of claim 10, further comprising measuring the thickness of the scar tissue before inserting the device comprising the array of solid glass micro-rods into the eye, and providing an array of solid glass micro-rods wherein the solid glass micro-rod length that is less than or equal to the thickness of the scar tissue.

12. The method of claim 10, wherein the measuring of the thickness of the scar tissue comprises optical coherence tomography (OCT) or Heidelberg retinal tomopgrapy.

13. The method of claim 10, wherein the engaging of the scar tissue or the underlying tissue on which the scar tissue is present with the sharp feature of the array of solid glass micro-rods comprises rotating the array of solid glass micro-rods about an axis that is substantially perpendicular to the surface of the scar tissue.

14. The method of claim 10, wherein the array of solid glass micro-rods comprise a silicon containing material.

15. The method of claim 10, wherein the length of the solid glass-micro-rod is less than 40 microns.

16. The method of claim 10, wherein the sharp feature of the solid glass micro-rods is angled from the plane that is normal to the face of the base of the array of solid glass micro rods, by an angle ranging from about 0 degrees to about 70 degrees.

* * * * *